United States Patent
Sode (10) Patent No.: US 7,049,114 B1
(45) Date of Patent: May 23, 2006

(54) GLUCOSE DEHYDROGENASE

(76) Inventor: Koji Sode, 1-13-16, Minami, Meguro-ku, Tokyo, 152-0013 (JP)

(*) Notice: Subject to any disclaimer, the term of this patent is extended or adjusted under 35 U.S.C. 154(b) by 0 days.

(21) Appl. No.: 09/959,549

(22) PCT Filed: May 1, 2000

(86) PCT No.: PCT/JP00/02872

§ 371 (c)(1),
(2), (4) Date: Oct. 30, 2001

(87) PCT Pub. No.: WO00/66744

PCT Pub. Date: Nov. 9, 2000

(30) Foreign Application Priority Data

Apr. 30, 1999 (JP) .................. 11-124285
Jan. 18, 2000 (JP) .................. 2000-009137

(51) Int. Cl.
*C12N 9/04* (2006.01)
*C12N 15/00* (2006.01)
*C12N 1/20* (2006.01)
*C12Q 1/00* (2006.01)
*C07H 21/04* (2006.01)

(52) U.S. Cl. .................. 435/190; 435/440; 435/4; 435/69.1; 435/183; 435/252.3; 435/320.1; 536/23.2; 536/23.7

(58) Field of Classification Search .............. 435/190, 435/440, 4; 536/23.2, 23.7
See application file for complete search history.

(56) References Cited

FOREIGN PATENT DOCUMENTS

JP 10-243786 9/1998

OTHER PUBLICATIONS

Database Swiss-Prot 'Online! Jan. 1, 1990 "Glucose dehydrogenase-B 'pyrroloquinoline-quinone! precursor" retrieved from Swiss-Prot Database accession No. P13650, XP002203013, *abstract*.

Oubrie Arthur et al.: "The 1.7 ANG crystal structure of the apo form of the soluble quinoprotein glucose dehydrogenase from Acinetobacter calcoaceticus reveals a novel internal conserved sequence repeat." Journal of Molecular Biology, vol. 289, No. 2, Jun. 4, 1999, pp. 319-333, XP002202799, ISSN: 0022-2836.

Oubrie Arthur et al.: "Active-site structure of the soluble quinoprotein glucose dehydrogenase complexed with methylhydrazine: A covalent cofactor-inhibitor complex." Proceedings of the National Academy of Sciences of the United States, vol. 96, No. 21, Oct. 12, 1999, pp. 11787-11791, XP002203011 Oct. 12, 1999, ISSN: 0027-8424.

(Continued)

*Primary Examiner*—Manjunath N. Rao
*Assistant Examiner*—Yong Pak
(74) *Attorney, Agent, or Firm*—Birch, Stewart, Kolasch & Birch, LLP (57) ABSTRACT

Modified water-soluble glucose dehydrogenases having pyrrolo-quinoline quinone as a coenzyme are provided wherein at least one amino acid residue is replaced by another amino acid residue in a specific region. Modified water-soluble PQQGDHs of the present invention have improved affinity for glucose.

10 Claims, 3 Drawing Sheets

OTHER PUBLICATIONS

Oubrie Arthur et al.: "Structural requirements of pyrroloquinoline quinone dependent enzymatic reactions." Protein Science, vol. 9, No. 7, Jul. 2000, pp. 1265-1273, XP002203012, ISSN: 0961-8368.

Igarashi S. et al.: "Construction and Characterization of mutant Water-Soluble PQQ Glucose Dehydrogenases with altered Km Values Site" Biochem. Biophys. Res. Commun. (Nov., 1999) vol. 264, No. 3, pp. 820-824.

Yoshida, H. et al.: "Engineering a chimeric pyrroloquinone glucose dehydrogenase: improvement of EDTA tolerance, thermal stability and substrate specificity" Protein Engineering (Jan., 1999) vol. 12, No. 1, pp. 63-70.

Clenton-Jansen, A. M. et al.: "Closing, characterization and DNA sequencing of the gene encoding the Mr. 50000 quinoprotein glucose dehydrogenase from Acinetobacter calcoaceticus" Mol. Genet. (1989) vol. 217, No. 2/3 pp. 430-436.

Mutant PQQGDH-B

FIG. 3

GLUCOSE DEHYDROGENASE

This application is the national phase under 35 U.S.C. § 371 of PCT International Application No. PCT/JP00/02872 which has an International filing date of May 1, 2000, which designated the United States of America and was not published in English.

TECHNICAL FIELD

The present invention relates to the preparation of glucose dehydrogenases having pyrrolo-quinoline quinone as a coenzyme (PQQGDH) and their use for glucose assays.

BACKGROUND ART

Blood glucose is an important marker for diabetes. In the fermentative production using microorganisms, glucose levels are assayed for monitoring the process. Conventional glucose assays were based on enzymatic methods using a glucose oxidase (GOD) or glucose-6-phosphate dehydrogenase (G6PDH). However, GOD-based assays required addition of a catalase or peroxidase to the assay system in order to quantitate the hydrogen peroxide generated by glucose oxidation reaction. G6PDHs have been used for spectrophotometric glucose assays, in which case a coenzyme NAD(P) had to be added to the reaction system.

Accordingly, an object of the present invention is to provide a modified water-soluble PQQGDH with improved affinity for glucose. Another object of the present invention is to provide a modified water-soluble PQQGDH with high selectivity for glucose in order to increase the sensitivity for measuring blood glucose levels.

DISCLOSURE OF THE INVENTION

We found that PQQGDHs with high affinity for glucose are useful as novel enzymes alternative to the enzymes that have been used for enzymatic glucose assays.

PQQGDHs are glucose dehydrogenases having pyrroloquinoline quinone as a coenzyme, which catalyze the reaction in which glucose is oxidized to produce gluconolactone.

PQQGDHs are known to include membrane-bound enzymes and water-soluble enzymes. Membrane-bound PQQGDHs are single peptide proteins having a molecular weight of about 87 kDa and widely found in various gram-negative bacteria. For example, see AM. Cleton-Jansen et al., J. Bacteriol. (1990) 172, 6308–6315. On the other hand, water-soluble PQQGDHs have been identified in several strains of *Acinetobacter calcoaceticus* (Biosci. Biotech. Biochem. (1995), 59(8), 1548–1555), and their structural genes were cloned to show the amino acid sequences (Mol. Gen. Genet. (1989), 217:430–436). The water-soluble PQQGDH derived from *A. calcoaceticus* is a homodimer having a molecular weight of about 50 kDa. It has little homology in primary structure of protein with other PQQ enzymes.

Recently, the results of an X-ray crystal structure analysis of this enzyme were reported to show the higher-order structure of the enzyme including the active center (J. Mol. Biol., 289, 319–333 (1999), The crystal structure of the apo form of the soluble quinoprotein glucose dehydrogenase from *Acinetobacter calcoaceticus* reveals a novel internal conserved sequence repeat; A. Oubrie et al., The EMBO Journal, 18(19) 5187–5194 (1999), Structure and mechanism of soluble quinoprotein glucose dehydrogenase, A. Oubrie et al., PNAS, 96(21), 11787–11791 (1999), Active-site structure of the soluble quinoprotein glucose dehydrogenase complexed with methylhydrazine; A covalent cofactor-inhibitor complex, A. Oubrie et al.). These papers showed that the water-soluble PQQGDH is a β-propeller protein composed of six W-motifs.

As a result of careful studies to develop a modified PQQGDH that can be applied to clinical tests or food analyses by improving the conventional water-soluble PQQGDH to increase the affinity for glucose, we succeeded in obtaining an enzyme with high affinity for glucose by introducing an amino acid change into a specific region of the water-soluble PQQGDH.

Accordingly, the present invention provides a modified water-soluble glucose dehydrogenase having pyrrolo-quinoline quinone as a coenzyme characterized in that at least one amino acid residue in a natural water-soluble glucose dehydrogenase is replaced by another amino acid residue and it has improved affinity for glucose as compared with the natural water-soluble glucose dehydrogenase. The modified PQQGDH of the present invention has a Km value for glucose lower than the Km value of the natural PQQGDH, preferably less than 20 mM, more preferably less than 10 mM.

Preferably, the modified glucose dehydrogenase of the present invention has increased affinity for glucose though its affinities for other sugars are unchanged or decreased, whereby it has higher selectivity for glucose than the natural water-soluble glucose dehydrogenase. Especially, the reactivity against lactose or maltose is decreased from that of the wild-type in contrast to the reactivity to glucose. When the reactivity against glucose is supposed to be 100%, the activity to lactose or maltose is preferably 60% or less, more preferably 50% or less, still more preferably 40% or less.

In an embodiment of the PQQ glucose dehydrogenase of the present invention, at least one amino acid residue in the region corresponding to residues 268–289 or 448–468 in the water-soluble PQQGDH derived from *Acinetobacter calcoaceticus* is replaced by another amino acid residue, i.e. an amino acid residue other than the relevant amino acid residue in the natural PQQ glucose dehydrogenase. The amino acid numbering herein starts from the initiator methionine as the +1 position.

The term "correspond to" used herein with reference to amino acid residues or regions means that some amino acid residues or regions have an equivalent function in two or more structurally similar but distinct proteins. For example, any region in water-soluble PQQGDHs derived from other organisms than *Acinetobacter calcoaceticus* is said to "correspond to the region defined by residues 268–289 in the water-soluble PQQGDH derived from *Acinetobacter calcoaceticus*" if this region has a high similarity in the amino acid sequence to the region defined by residues 268–289 in the water-soluble PQQGDH derived from *Acinetobacter calcoaceticus* and this region is reasonably considered from the secondary structure of the protein to have the same function in that protein. In addition, the 10th amino acid residue in this region is said to "correspond to the 277th residue in the water-soluble PQQGDH derived from *Acinetobacter calcoaceticus*".

In preferred modified PQQGDHs of the present invention, at least one amino acid residue corresponding to glutamate 277, isoleucine 278, asparagine 462, asparagine 452, lysine 455, aspartate 456, aspartate 457 or aspartate 448 in the amino acid sequence shown as SEQ ID NO: 1 is replaced by another amino acid residue.

In more preferred modified PQQGDHs of the present invention, glutamate 277 is replaced by an amino acid residue selected from the group consisting of alanine, asparagine, lysine, aspartate, histidine, glutamine, valine and glycine, or isoleucine 278 is replaced by phenylalanine in the amino acid sequence shown as SEQ ID NO: 1.

In another aspect, modified PQQGDHs of the present invention comprise the sequence (SEQ ID NO: 14):
Xaa8 Thr Ala Gly Xaa1 Val Gln Xaa2 Xaa3 Xaa4 Gly Ser Val Thr Xaa5 Thr Leu Glu Asn Pro Gly wherein Xaa1, Xaa2, Xaa3, Xaa4, Xaa5 and Xaa8 represent any natural amino acid residue, provided that when Xaa1 represents Asn, Xaa2 represents Lys, Xaa3 represents Asp, Xaa4 represents Asp and Xaa5 represents Asn, then Xaa8 does not represent Asp.

In another aspect, modified PQQGDHs of the present invention comprise the sequence (SEQ ID NO: 3):
Ser Glu Gln Gly Pro Asn Ser Asp Asp Xaa6 Xaa7 Asn Leu Ile Val Lys Gly Gly Asn Tyr Gly Trp wherein Xaa6 and Xaa7 represent any natural amino acid residue, provided that when Xaa6 represents Glu, Xaa7 does not represent Ile.

The present invention also provides a gene encoding any of the modified glucose dehydrogenases described above, a vector containing said gene and a transformant containing said gene, as well as a glucose assay kit and a glucose sensor comprising a modified glucose dehydrogenase of the present invention.

Enzyme proteins of modified PQQGDHs of the present invention have high affinity for glucose and high oxidation activity for glucose so that they can be applied to highly sensitive and highly selective glucose assays.

THE MOST PREFERRED EMBODIMENTS OF THE INVENTION

Structure of Modified POOGDHs

We introduced random mutations into the coding region of the gene encoding the water-soluble PQQGDH by error-prone PCR to construct a library of water-soluble PQQGDHs carrying amino acid changes. These genes were transformed into *E. coli* and screened for the activity of the PQQGDHs against glucose to give a number of clones that express PQQGDHs having comparable activities for 20 mM glucose and 100 mM glucose and improved reactivity against low-level glucose as compared with that of the wild-type enzyme.

Analysis of the nucleotide sequence of one of these clones showed that Glu 277 had been changed to Gly. When this amino acid residue was replaced by various other amino acid residues, excellent mutant enzymes with improved affinity for glucose as compared with that of the wild type water-soluble PQQGDH were obtained in every case.

Then, site-specific mutations were introduced into other residues near the 277th residue and the affinity for glucose was determined. Modified enzymes carrying Ile278Phe and Asn279His in the region defiend by residues 268–289 were prepared and assayed for the activity to show that these modified enzymes had high affinity for glucose.

A number of clones obtained as above were further screened for clones that express PQQGDHs having activity for 20 mM glucose comparable to that of the wild-type PQQGDH but activity for 20 mM lactose lower than that of the wild-type PQQGDH.

Analysis of the nucleotide sequence of one of these clones showed that Asn 452 had been changed to Asp. When this residue was replaced by threonine, lysine, isoleucine, histidine or aspartate, excellent mutant enzymes with improved selectivity for glucose as compared with that of the wild type water-soluble PQQGDH were obtained in every case. Mutations were also introduced into other residues near the 452nd residue in the same manner. Mutant enzymes carrying Lys455Ile, Asp456Asn, Asp457Asn, Asn462Asp, Asp448Asn were constructed. As a result, all the mutant enzymes were found to have improved selectivity for glucose as shown in Table 4.

In preferred PQQ glucose dehydrogenases of the present invention, at least one amino acid residue is replaced by another amino acid residue in the region corresponding to residues 448–468 in the water-soluble PQQGDH derived from *Acinetobacter calcoaceticus*. In preferred modified PQQGDHs of the present invention, at least one amino acid residue corresponding to asparagine 462, lysine 452, aspartate 456, aspartate 457 or aspartate 448 in the amino acid sequence shown as SEQ ID NO: 1 is replaced by another amino acid residue.

In another aspect, modified PQQGDHs of the present invention comprise the sequence (SEQ ID NO: 14):
Xaa8 Thr Ala Gly Xaa1 Val Gln Xaa2 Xaa3 Xaa4 Gly Ser Val Thr Xaa5 Thr Leu Glu Asn Pro Gly wherein Xaa1, Xaa2, Xaa3, Xaa4, Xaa5 and Xaa8 represent any natural amino acid residue, provided that when Xaa1 represents Asn, Xaa2 represents Lys, Xaa3 represents Asp, Xaa4 represents Asp and Xaa5 represents Asn, then Xaa8 does not represent Asp.

In other preferred PQQ glucose dehydrogenases of the present invention, at least one amino acid residue is replaced by another amino acid residue in the region corresponding to residues 268–289 in the amino acid sequence shown as SEQ ID NO: 1. In especially preferred modified PQQGDHs of the present invention, glutamate 277 is replaced by an amino acid residue selected from the group consisting of alanine, asparagine, lysine, aspartate, histidine, glutamine, valine and glycine, or isoleucine 278 is replaced by phenylalanine in the amino acid sequence shown as SEQ ID NO: 1.

In another aspect, modified PQQGDHs of the present invention comprise the sequence (SEQ ID NO: 3):
Ser Glu Gln Gly Pro Asn Ser Asp Asp Xaa6 Xaa7 Asn Leu Ile Val Lys Gly Gly Asn Tyr Gly Trp wherein Xaa6 and Xaa7 represent any natural amino acid residue, provided that when Xaa6 represents Glu, Xaa7 does not represent Ile.

In modified glucose dehydrogenases of the present invention, other amino acid residues may be partially deleted or substituted or other amino acid residues may be added so far as glucose dehydrogenase activity is retained.

Those skilled in the art can also replace an amino acid residue in water-soluble PQQGDHs derived from other bacteria according to the teaching herein to obtain modified glucose dehydrogenases with improved affinity for glucose. Particularly, amino acid residues corresponding to glutamate 277, isoleucine 278, asparagine 462, lysine 452, aspartate 455, aspartate 456, aspartate 457 and aspartate 448 in the water-soluble PQQGDH derived from *Acinetobacter calcoaceticus* can be readily identified by comparing the primary structures of proteins in alignment or comparing the secondary structures predicted from the primary structures of the enzymes. Modified glucose dehydrogenases with improved affinity for substrate can be obtained by replacing such amino acid residues according to the present invention. These modified glucose dehydrogenases are also within the scope of the present invention.

Process for Preparing Modified POOGDHs

The sequence of the gene encoding the wild-type water-soluble PQQGDH derived from *Acinetobacter calcoaceticus* is defined by SEQ ID NO: 2.

Genes encoding modified PQQGDHs of the present invention can be constructed by replacing the nucleotide sequence encoding a specific amino acid residue in the gene encoding the wild-type water-soluble PQQGDH by the nucleotide sequence encoding an amino acid residue to be substituted. Various techniques for such site-specific nucleotide sequence substitution are known in the art as described in Sambrook et al., "Molecular Cloning: A Laboratory Manual", Second Edition, 1989, Cold Spring Harbor Laboratory Press, New York, for example.

Thus obtained mutant gene is inserted into a gene expression vector (for example, a plasmid) and transformed into an appropriate host (for example, *E. coli*). A number of vector/host systems for expressing a foreign protein are known and various hosts such as bacteria, yeasts or cultured cells are suitable.

Random mutations are introduced by error-prone PCR into a target region to construct a gene library of modified water-soluble PQQGDHs carrying mutations in the target region. These genes are transformed into *E. coli* to screen each clone for the affinity of the PQQGDH for glucose. Water-soluble PQQGDHs are secreted into the periplasmic space when they are expressed in *E. coli*, so that they can be easily assayed for enzyme activity using the *E. coli* cells. This library is combined with a PMS-DCIP dye in the presence of 20 mM glucose to visually determine the PQQGDH activity so that clones showing activity comparable to the activity for 100 mM glucose are selected and analyzed for the nucleotide sequence to confirm the mutation.

In order to obtain modified PQQGDHs with improved selectivity for glucose, this library is combined with a PMS-DCIP dye to visually determine the PQQGDH activity so that clones showing activity for 20 mM glucose comparable to that of the wild-type PQQGDH but activity for 20 mM lactose lower than that of the wild-type PQQGDH are selected and analyzed for the nucleotide sequence to confirm the mutation.

Thus obtained transformed cells expressing modified PQQGDHs are cultured and harvested by centrifugation or other means from the culture medium, and then disrupted with a French press or osmotically shocked to release the periplasmic enzyme into the medium. The enzyme may be ultracentrifuged to give a water-soluble PQQGDH-containing fraction. Alternatively, the expressed PQQGDH may be secreted into the medium by using an appropriate host/vector system. The resulting water-soluble fraction is purified by ion exchange chromatography, affinity chromatography, HPLC and the like to prepare a modified PQQGDH of the present invention.

Method for Assaying Enzyme Activity

PQQGDHs of the present invention associate with PQQ as a coenzyme in catalyzing the reaction in which glucose is oxidized to produce gluconolactone.

The enzyme activity can be assayed by using the color-developing reaction of a redox dye to measure the amount of PQQ reduced with PQQGDH-catalyzed oxidation of glucose. Suitable color-developing reagents include PMS (phenazine methosulfate)-DCIP (2,6-dichlorophenolindophenol), potassium ferricyanide and ferrocene, for example.

Affinity for Glucose

Modified PQQGDHs of the present invention have greatly improved affinity for glucose as compared with that of the wild type. Thus, modified PQQGDHs have a Km value for glucose that is greatly lower than the Km value for glucose of the wild-type PQQGDH. Among modified PQQGDHs, the Glu277Lys variant has a Km value for glucose of 8.8 mM and a maximum activity comparable to that of the wild-type enzyme so that it has improved reactivity against glucose at low levels.

Therefore, assay kits or enzyme sensors prepared with modified enzymes of the present invention have the excellent advantages that they can detect glucose at low levels because of the high sensitivity for glucose assays.

Evaluation Method of Selectivity

Selectivity for glucose of PQQGDHs of the present invention can be evaluated by assaying the enzyme activity as described above using various sugars such as 2-deoxy-D-glucose, mannose, allose, 3-o-methyl-D-glucose, galactose, xylose, lactose and maltose as substrates and determining the relative activity to the activity for glucose.

Glucose Assay Kit

The present invention also relates to a glucose assay kit comprising a modified PQQGDH according to the present invention. The glucose assay kit of the present invention comprises a modified PQQGDH according to the present invention in an amount enough for at least one run of assay. In addition to the modified PQQGDH according to the present invention, the kit typically comprises a necessary buffer for the assay, a mediator, standard glucose solutions for preparing a calibration curve and instructions. Modified PQQGDHs according to the present invention can be provided in various forms such as freeze-dried reagents or solutions in appropriate preservative solutions. Modified PQQGDHs according to the present invention are preferably provided in the form of a holoenzyme, though they may also be provided as an apoenzyme and converted into a holoenzyme before use.

Glucose Sensor

The present invention also relates to a glucose sensor using a modified PQQGDH according to the present invention. Suitable electrodes include carbon, gold, platinum and the like electrodes, on which an enzyme of the present invention is immobilized by using a crosslinking agent; encapsulation in a polymer matrix; coating with a dialysis membrane; using a photo-crosslinkable polymer, an electrically conductive polymer or a redox polymer; fixing the enzyme in a polymer or adsorbing it onto the electrode with an electron mediator including ferrocene or its derivatives; or any combination thereof. Modified PQQGDHs of the present invention are preferably immobilized in the form of a holoenzyme on an electrode, though they may be immobilized as an apoenzyme and PQQ may be provided as a separate layer or in a solution. Typically, modified PQQGDHs of the present invention are immobilized on a carbon electrode with glutaraldehyde and then treated with an amine-containing reagent to block glutaraldehyde.

Glucose levels can be measured as follows. PQQ, $CaCl_2$ and a mediator are added to a thermostat cell containing a buffer and kept at a constant temperature. Suitable mediators include, for example, potassium ferricyanide and phenazine methosulfate. An electrode on which a modified PQQGDH of the present invention has been immobilized is used as a working electrode in combination with a counter electrode (e.g. a platinum electrode) and a reference electrode (e.g. an Ag/AgCl electrode). After a constant voltage is applied to the carbon electrode to reach a steady current, a glucose-containing sample is added to measure the increase in current. The glucose level in the sample can be calculated from a calibration curve prepared with glucose solutions at standard concentrations.

The disclosures of all the patents and documents cited herein are entirely incorporated herein as reference. The present application claims priority based on Japanese Patent Applications Nos. 1999–124285 and 2000–9137, the disclosure of which is entirely incorporated herein as reference.

The following examples further illustrate the present invention without, however, limiting the same thereto.

EXAMPLE 1

Figure 1:
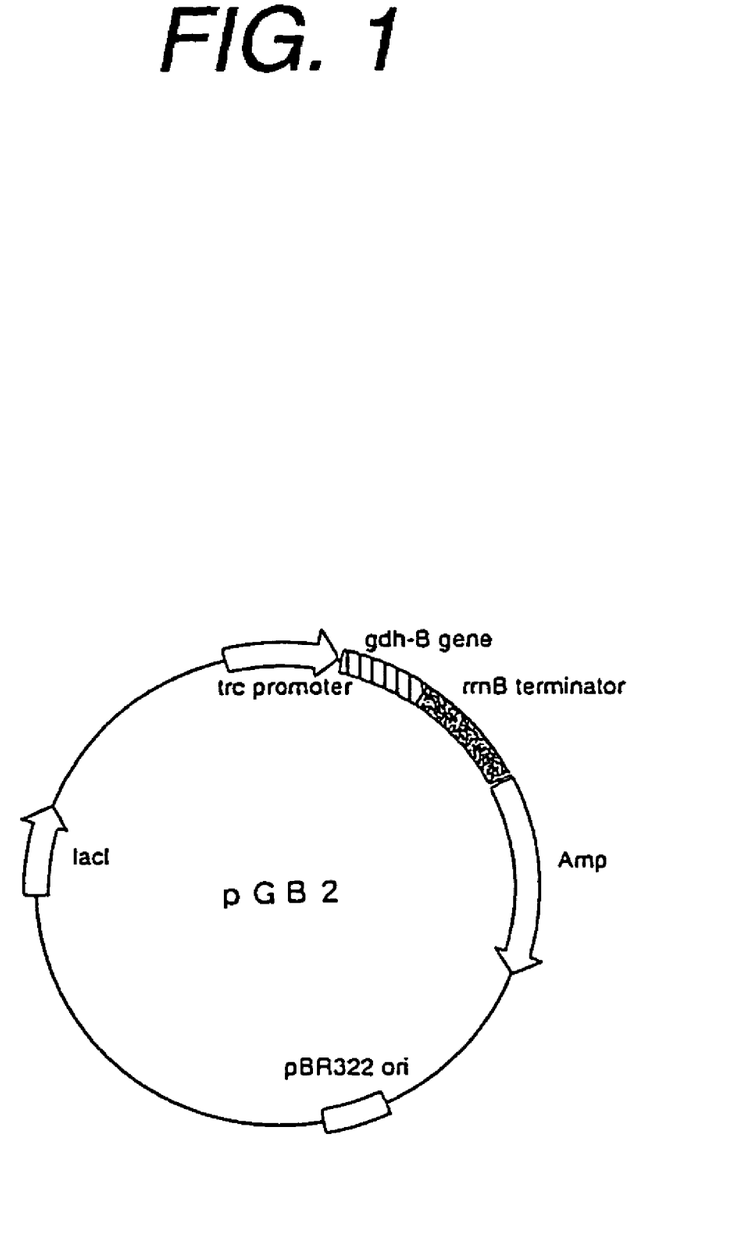
FIG. 1 shows the structure of the plasmid pGB2 used in the present invention.

Construction and Screening of a Mutant PQQGDH Gene Library:

The plasmid pGB2 was obtained by inserting the structural gene encoding the PQQGDH derived from *Acinetobacter calcoaceticus* into the multicloning site of the vector pTrc99A (Pharmacia) (FIG. 1). This plasmid was used as a template to introduce random mutations into various regions by error-prone PCR. The PCR reaction was carried out in a solution having the composition shown in Table 1 under the conditions of 94° C. for 3 minutes, 30 cycles of 94° C. for 3 minutes, 50° C. for 2 minutes and 72° C. for 2 minutes, and finally 72° C. for 10 minutes.

TABLE 1

| | |
|---|---|
| TaqDNA polymerase (5U/μl) | 0.5 μl |
| Template DNA | 1.0 μl |
| Forward primer ABF | 4.0 μl |
| Reverse primer ABR | 4.0 μl |
| 10 × Taq polymerase buffer | 10.0 μl |
| 1M β-mercaptoethanol | 1.0 μl |
| DMSO | 10.0 μl |

TABLE 1-continued

| | |
|---|---|
| 5 mM $MnCl_2$ | 10.0 μl |
| 10 mM dGTP | 2.0 μl |
| 2 mM dATP | 2.0 μl |
| 10 mM dCTP | 2.0 μl |
| 10 mM dTTP | 2.0 μl |
| $H_2O$ | 51.5 μl |
| | 100.0 μl |

The resulting mutant water-soluble PQQGDH library was transformed into *E. coli* and each colony formed was transferred to a microtiter plate. The colony was further replica-plated on a first plate containing 10 mM glucose and PMS-DCIP and a second plate containing 100 mM glucose and PMS-CDIP, and both were visually evaluated for the PQQGDH activity. A number of clones showing comparable PQQGDH activities in both plates were obtained.

One of these clones was randomly selected and analyzed for the nucleotide sequence to show that glutamate 277 had been changed to glycine.

EXAMPLE 2

Each colony obtained in Example 1 was transferred to a microtiter plate. The colony was replica-plated on a first plate containing 20 mM glucose and PMS-DCIP and a second plate containing 20 mM lactose and PMS-CDIP, and both were visually evaluated for the PQQGDH activity. A number of clones showing a greatly lower activity for lactose than glucose in both plates were obtained.

One of these clones was randomly selected and analyzed for the nucleotide sequence to show that asparagine 452 had been changed to aspartate.

EXAMPLE 3

Figure 2:
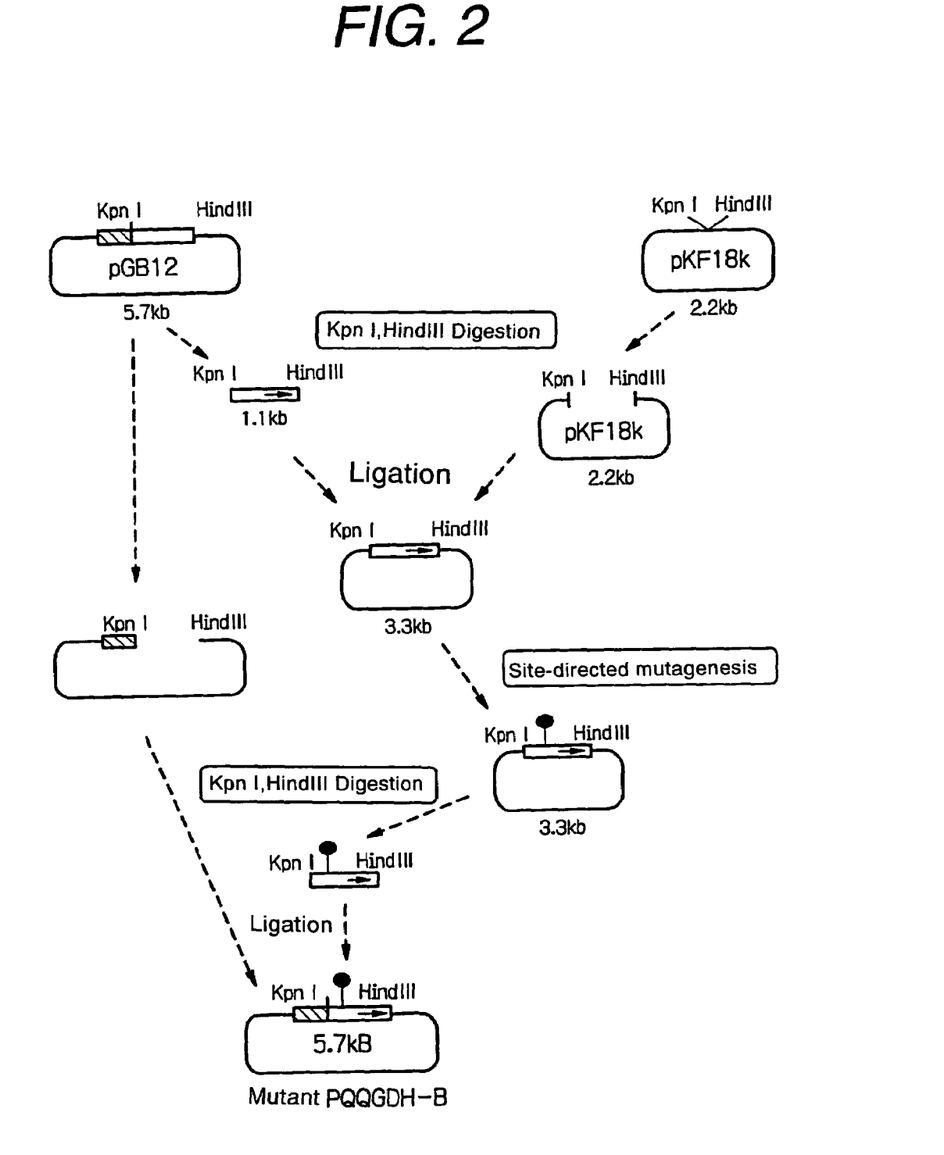
FIG. 2 shows a scheme for preparing a mutant gene encoding a modified enzyme of the present invention.

Construction of Modified PQQGDH Genes:

Based on the structural gene of the PQQGDH derived from *Acinetobacter calcoaceticus* shown as SEQ ID NO: 2, the nucleotide sequence encoding glutamate 277 or isoleucine 278 was replaced by the nucleotide sequences encoding given amino acid residues by site-directed mutagenesis according to a standard method as shown in FIG. 2 using the plasmid pGB2. Table 2 shows the sequences of the synthetic oligonucleotide target primers used for mutagenesis. In Table 2, "E277A" means that glutamate 277 is replaced by aspartate, for example.

TABLE 2

| | | |
|---|---|---|
| (SEQ ID NO: 4) | E277A 5'- | GAG GTT AAT TGC ATC GTC AGA G -3' |
| (SEQ ID NO: 5) | E277N 5'- | C AAT GAG GTT AAT GTT ATC GTC AGA GTT TG-3' |
| (SEQ ID NO: 6) | E277K 5'- | GAG GTT AAT ATC ATC GTC AGA G -3' |
| (SEQ ID NO: 7) | E277D 5'- | GAG GTT AAT TTT ATC GTC AGA G -3' |
| (SEQ ID NO: 8) | E277H 5'- | C AAT GAG GTT AAT GTG ATC GTC AGA GTT TG-3' |
| (SEQ ID NO: 9) | E277Q 5'- | GAG GTT AAT TTG ATC GTC AGA G -3' |
| (SEQ ID NO: 10) | E277V 5'- | C AAT GAG GTT AAT TAC ATC GTC AGA GTT TG-3' |
| (SEQ ID NO: 11) | E277G 5'- | GAG GTT AAT TCC ATC GTC AGA G -3' |

TABLE 2-continued (SEQ ID NO: 12) I278F 5'- C AAT GAG GTT GAA TTC ATC GTC AGA G   -3'

(SEQ ID NO: 13) N279H 5'-GAC AAT GAG GTG AAT TTC ATC GTC AGA GTT -3'

A KpnI-HindIII fragment containing a part of the gene encoding the PQQGDH derived from *Acinetobacter calcoaceticus* was integrated into the vector plasmid pKF18k (Takara Shuzo Co., Ltd.) and used as a template. Fifty fmols of this template, 5 pmol of the selection primer attached to the Mutan™-Express Km Kit (Takara Shuzo Co., Ltd.) and 50 pmol of the phosphorylated target primer were mixed with the annealing buffer attached to the kit in an amount equivalent to 1/10 of the total volume (20 µl), and the mixture was heated at 100° C. for 3 minutes to denature the plasmid into a single strand. The selection primer serves for reversion of dual amber mutations on the kanamycin-resistance gene of pKF18k. The mixture was placed on ice for 5 minutes to anneal the primers. To this mixture were added 3 µl of the extension buffer attached to the kit, 1 µl of T4 DNA ligase, 1 µl of T4 DNA polymerase and 5 µl of sterilized water to synthesize a complementary strand.

The synthetic strand was transformed into a DNA mismatch repair-deficient strain *E. coli* BMH71–18mutS and shake-cultured overnight to amplify the plasmid.

Then, the plasmid copies were extracted from the cultures and transformed into *E. coli* MV1184 and then extracted from the colonies. These plasmids were sequenced to confirm the introduction of the intended mutations. These fragments were substituted for the KpnI-HindIII fragment of the gene encoding the wild-type PQQGDH on the plasmid pGB2A to construct genes for modified PQQGDHs.

An oligonucleotide target primer of the sequence (SEQ ID NO: 15):

5'-C ATC TTT TTG GAC ATG TCC GGC AGT AT-3' was synthesized in the same manner to substitute histidine for asparagine 452. Site-directed mutagenesis was performed by the method shown in FIG. 2 using the plasmid pGB2. Genes for modified PQQGDHs carrying mutations Asp448Asn, Asn452Asp, Asn452His, Asn452Lys, Asn452Thr, Asn452Ile, Lys455Ile, Asp456Asn, Asp457Asn and Asn462Asp were also constructed.

EXAMPLE 4

Preparation of Modified Enzymes

The gene encoding the wild-type or each modified PQQGDH was inserted into the multicloning site of an *E. coli* expression vector pTrc99A (Pharmacia), and the resulting plasmid was transformed into the *E. coli* strain DH5α. The transformant was shake-cultured at 37° C. overnight on 450 ml of L medium (containing 50 µg/ml of ampicillin) in a Sakaguchi flask, and inoculated on 7 l of L medium containing 1 mM $CaCl_2$ and 500 µM PQQ. About 3 hours after starting cultivation, isopropyl thiogalactoside was added at a final concentration of 0.3 mM, and cultivation was further continued for 1.5 hours. The cultured cells were harvested from the medium by centrifugation (5,000×g, 10 min, 4° C.), and washed twice with a 0.85% NaCl solution. The collected cells were disrupted with a French press, and centrifuged (10,000×g, 15 min, 4° C.) to remove undisrupted cells. The supernatant was ultracentrifuged (160,500×g (40,000 r.p.m.), 90 min, 4° C.) to give a water-soluble fraction, which was used in the subsequent examples as a crude enzyme sample.

Thus obtained water-soluble fraction was further dialyzed against 10 mM phosphate buffer, pH 7.0 overnight. The dialyzed sample was adsorbed to a cation chromatographic column TSKgel CM-TOYOPEARL 650M (Tosoh Corp.), which had been equilibrated with 10 mM phosphate buffer, pH 7.0. This column was washed with 750 ml of 10 mM phosphate buffer, pH 7.0 and then the enzyme was eluted with 10 mM phosphate buffer, pH 7.0 containing 0–0.2 M NaCl at a flow rate of 5 ml/min. Fractions having GDH activity were collected and dialyzed against 10 mM MOPS-NAOH buffer, pH 7.0 overnight. Thus, an electrophoretically homogeneous modified PQQGDH protein was obtained. This was used in the subsequent examples as a purified enzyme sample.

EXAMPLE 5

Assay of Enzyme Activity:

Enzyme activity was assayed by using PMS (phenazine methosulfate)-DCIP (2,6-dichlorophenolindophenol) in 10 mM MOPS-NaOH buffer (pH 7.0) to monitor changes in the absorbance of DCIP at 600 nm with a spectrophotometer and expressing the reaction rate of the enzyme as the rate of decrease in the absorbance. The enzyme activity for reducing 1 µmol of DCIP in 1 minute was 1 U. The molar extinction coefficient of DCIP at pH 7.0 was 16.3 $mM^{-1}$.

EXAMPLE 6

Evaluation of Affinity of Crude Enzyme Samples for Glucose:

Each of the crude enzyme samples of the wild-type and modified PQQGDHs obtained in Example 4 was converted into a holoenzyme in the presence of 1 µM PQQ and 1 mM $CaCl_2$ for 1 hour or longer. A 187 µl-aliquot was combined with 3 µl of an activating reagent (prepared from 48 µl of 6 mM DCIP, 8 µl of 600 mM PMS and 16 µl of 10 mM phosphate buffer, pH 7.0) and 10 µl of D-glucose solutions at various concentrations, and assayed for the enzyme activity at room temperature by the method shown in Example 5. The Km was determined by plotting the substrate concentration vs. enzyme activity. The results are shown in Table 3.

TABLE 3

|           | Km (mM) |
|-----------|---------|
| Wild type | 26.0    |
| E277A     | 1.5     |
| E277N     | 1.2     |
| E277K     | 8.9     |
| E277D     | 7.4     |
| E277H     | 7.7     |
| E277Q     | 4.3     |

TABLE 3-continued

| | Km (mM) |
|---|---|
| E277V | 2.5 |
| E277G | 0.3 |
| I278F | 7.0 |
| N279H | 15.7 |
| N452T | 12.5 |
| N462D | 12.2 |
| N462K | 11.0 |
| N462Y | 20.4 |

The Km value of the wild-type PQQGDH for glucose reported to date was about 25 mM. In contrast, all the enzymes constructed here to carry mutations in glutamate 277 and Ile278Phe had a Km value for glucose of less than 10 mM. These results show that modified PQQGDHs of the present invention have high affinity for glucose.

EXAMPLE 7

Evaluation of Affinity of Purified Enzyme Samples for Glucose:

Each of the purified samples of the wild-type enzyme and the modified enzyme Glu277Lys obtained in Example 4 was converted into a holoenzyme in the presence of 1 µM PQQ and 1 mM CaCl₂ for 1 hour or longer in the same manner as in Example 6. A 187 µl-aliquot was combined with 3 µl of an activating reagent (prepared from 48 µl of 6 mM DCIP, 8 µl of 600 mM PMS and 16 µl of 10 mM phosphate buffer, pH 7.0) and 10 µl of D-glucose solutions at various concentrations, and assayed for the enzyme activity at room temperature by the method shown in Example 5. The Km and Vmax were determined by plotting the substrate concentration vs. enzyme activity. The Glu277Lys variant had a Km value for glucose of about 8.8 mM and a Vmax value of 3668 U/mg. The Km value of the wild-type PQQGDH for glucose reported to date was about 25 mM with the Vmax value being 2500–7000 U/mg depending on the measurement conditions. These results show that the modified PQQGDH Glu277Lys is an enzyme having remarkably improved affinity for glucose and high activity comparable to that of the wild-type PQQGDH.

EXAMPLE 8

Evaluation of Substrate Specificity:

Crude samples of various modified enzymes were tested for substrate specificity. Each of the crude samples of the wild-type and various modified PQQGDHs was converted into a holoenzyme in the presence of 1 µM PQQ and 1 mM CaCl₂ for 1 hour or longer. A 187 µl-aliquot was combined with 3 µl of an activating reagent (containing 6 mM DCIP, 600 mM PMS and 10 mM phosphate buffer, pH 7.0) and a substrate. The substrates tested were 400 mM glucose, lactose and maltose at a final concentration of 20 mM, and each sample was incubated with 10 µl of each substrate at room temperature for 30 minutes and assayed for the enzyme activity in the same manner as in Example 5 to determine the relative activity expressed as the percentage of the activity for glucose. As shown in Table 4, all the modified enzymes of the present invention showed higher selectivity for glucose than that of the wild-type enzyme.

TABLE 4

| | Glucose | Lactose | Maltose |
|---|---|---|---|
| Wild-type | 100% | 61% | 61% |
| Asp448Asn | 100% | 48% | 36% |
| Asn452Asp | 100% | 56% | 50% |
| Asn452His | 100% | 39% | 39% |
| Asn452Lys | 100% | 55% | 42% |
| Asn452Thr | 100% | 42% | 30% |
| Asn452Ile | 100% | 36% | 28% |
| Lys455Ile | 100% | 49% | 37% |
| Asp456Asn | 100% | 59% | 41% |
| Asp457Asn | 100% | 43% | 32% |
| Asn462Asp | 100% | 52% | 41% |

EXAMPLE 9

Figure 3:
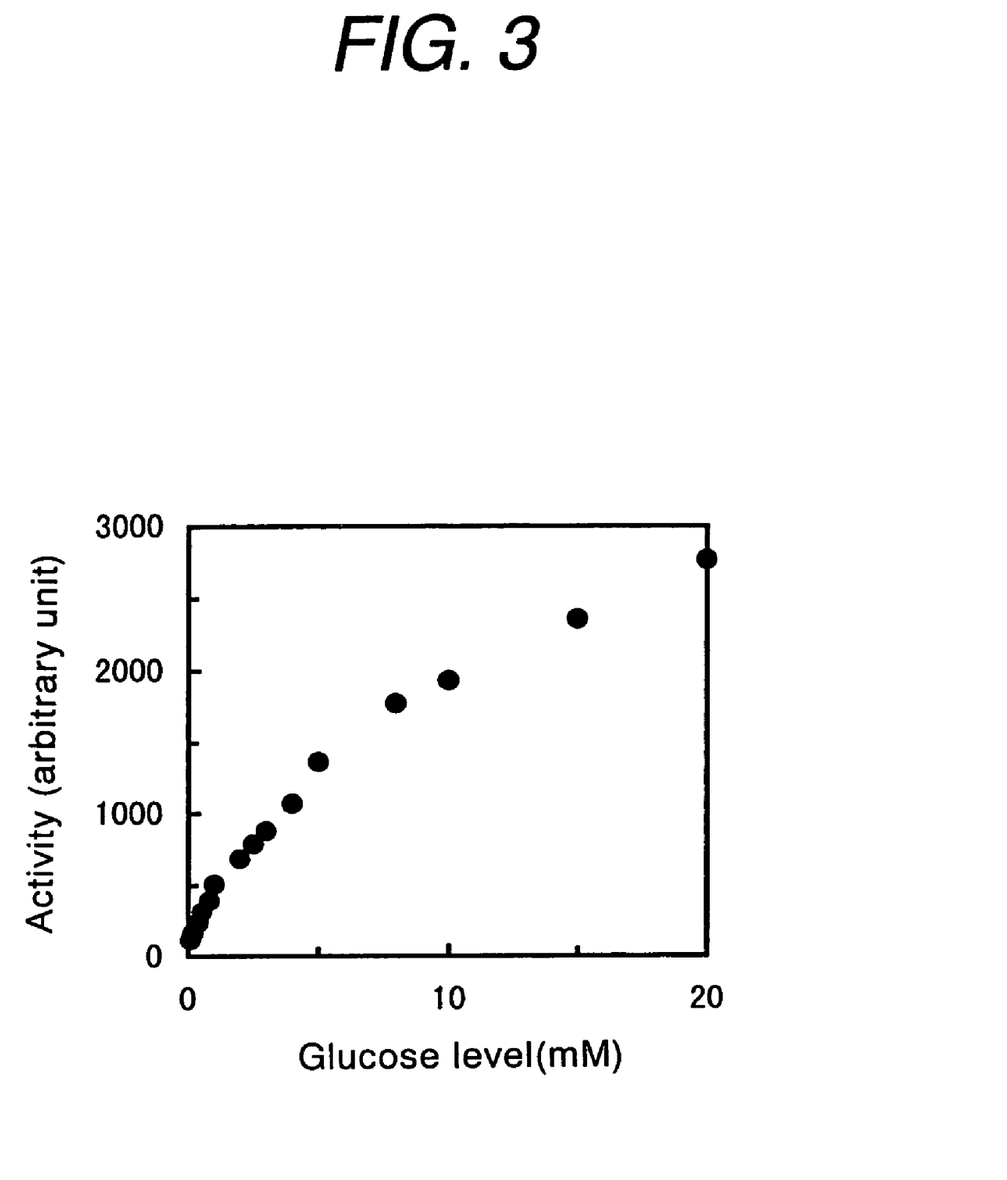
FIG. 3 shows a glucose assay using a modified PQQGDH of the present invention.

Glucose Assay:

Modified PQQGDHs were used for assaying glucose. Each of the modified enzymes Glu277Lys and Asn452Thr was converted into a holoenzyme in the presence of 1 µM PQQ and 1 mM CaCl₂ for 1 hour or longer, and assayed for the enzyme activity in the presence of glucose at various concentrations as well as 5 µM PQQ and 10 mM CaCl₂ by the method described in Example 5 based on changes of the absorbance of DCIP at 600 nm. As shown in FIG. 3, the modified PQQGDH Asn452Thr could be used for assaying glucose in the range of 0.1–20 mM. Similar results were obtained with the modified PQQGDH Glu277Lys.

EXAMPLE 10

Preparation and Evaluation of an Enzyme Sensor:

Five units each of the modified enzymes Glu277Lys and Asn452Thr were freeze-dried with 20 mg of carbon paste. After thorough mixing, the mixture was applied only on the surface of a carbon paste electrode preliminarily filled with about 40 mg of carbon paste and polished on a filter paper. This electrode was treated in 10 mM MOPS buffer (pH 7.0) containing 1% glutaraldehyde at room temperature for 30 minutes followed by 10 mM MOPS buffer (pH 7.0) containing 20 mM lysine at room temperature for 20 minutes to block glutaraldehyde. The electrode was equilibrated in 10 mM MOPS buffer (pH 7.0) at room temperature for 1 hour or longer and then stored at 4° C.

Thus prepared enzyme sensor was used to measure glucose levels. The enzyme sensor having a modified PQQGDH of the present invention immobilized thereon can be used for assaying glucose in the range of 0.1 mM–5 mM.

INDUSTRIAL APPLICABILITY

Modified PQQGDHs of the present invention have high affinity for glucose so that they are expected to provide the advantages that assay kits or enzyme sensors prepared with such enzymes can measure glucose at lower levels with remarkably improved sensitivity as compared with conventional natural PQQGDHs.

The invention claimed is:

1. An isolated mutant glucose dehydrogenase consisting of the amino acid sequence of SEQ ID NO:1 and having pyrrolo-quinoline quinone as a coenzyme, wherein said mutant consists of one mutation, a substitution of asparagine at position 438 with aspartate, and wherein said mutant has glucose dehydrogenase activity.

2. An isolated modified mutant glucose dehydrogenase consisting of the amino acid sequence of SEQ ID NO:1 and having pyrrolo-quinoline quinone as a coenzyme, wherein said mutant consists of one mutation, a substitution of asparagine at position 428 with threonine, lysine, isoleucine, histidine or aspartate, and wherein said mutant has glucose dehydrogenase activity.

3. An isolated mutant glucose dehydrogenase consisting of the amino acid sequence of SEQ ID NO:1 and having pyrrolo-quinoline quinone as a coenzyme, wherein said mutant consists of one mutation, a substitution of lysine at position 431 with isoleucine, and wherein said mutant has glucose dehydrogenase activity.

4. An isolated mutant glucose dehydrogenase consisting of the amino acid sequence of SEQ ID NO:1 and having pyrrolo-quinoline quinone as a coenzyme, wherein said mutant consists of one mutation, a substitution of aspartate at position 432 with asparagine, and wherein said mutant has glucose dehydrogenase activity.

5. An isolated mutant glucose dehydrogenase consisting of the amino acid sequence of SEQ ID NO:1 and having pyrrolo-quinoline quinone as a coenzyme, wherein said mutant consists of one mutation, a substitution of aspartate at position 433 with asparagine, and wherein said mutant has glucose dehydrogenase activity.

6. An isolated mutant glucose dehydrogenase consisting of the amino acid sequence of SEQ ID NO:1 and having pyrrolo-quinoline quinone as a coenzyme, wherein said mutant consists of one mutation, a substitution of aspartate at position 424 with asparagine, and wherein said mutant has glucose dehydrogenase activity.

7. An isolated mutant glucose dehydrogenase consisting of the amino acid sequence of SEQ ID NO:1 and having pyrrolo-quinoline quinone as a coenzyme, wherein said mutant consists of one mutation, a substitution of glutamate at position 253 with alanine, asparagine, lysine, aspartate, histidine, glutamine, valine or glycine, and wherein said mutant has glucose dehydrogenase activity.

8. An isolated mutant water-soluble glucose dehydrogenase consisting of the amino acid sequence of SEQ ID NO:1 and having pyrrolo-quinoline quinone as a coenzyme, wherein said mutant consists of one mutation, a substitution of isoleucine at position 254 with phenylalanine, and wherein said mutant has glucose dehydrogenase activity.

9. An isolated mutant water-soluble glucose dehydrogenase consisting of the amino acid sequence of SEQ ID NO:1 and having pyrrolo-quinoline quinone as a coenzyme, wherein said mutant consists of one mutation, a substitution of asparagine at position 255 with histidine, and wherein said mutant has glucose dehydrogenase activity.

10. An isolated mutant glucose dehydrogenase consisting of the amino acid sequence of SEQ ID NO:1 and having pyrrolo-quinoline quinone as a coenzyme, wherein said mutant consists of at least one mutation selected from the group consisting of:
  (1) asparagine at position 438 substituted with aspartate,
  (2) asparagine at position 428 substituted with threonine, lysine, isoleucine, histidine or aspartate;
  (3) lysine at position 431 substituted with isoleucine,
  (4) aspartate at position 432 substituted with asparagine;
  (5) aspartate at position 433 substituted with asparagine;
  (6) aspartate at position 424 substituted with asparagine;

(7) glutamate at position 253 substituted with alanine, asparagine, lysine, aspartate, histidine, glutamine, valine or glycine;
(8) isoleucine at position 254 substituted with phenylalanine; and
(9) asparagine at position 255 substituted with histidine, and wherein said mutant has glucose dehydrogenase activity.

* * * * *

SEQUENCE LISTING

<160> NUMBER OF SEQ ID NOS: 15

<210> SEQ ID NO 1
<211> LENGTH: 454
<212> TYPE: PRT
<213> ORGANISM: Acinetobacter calcoaceticus

<400> SEQUENCE: 1

```
Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ala Asn Lys
        275                 280                 285

Ser Ile Lys Asp Leu Ala Gln Asn Gly Val Lys Val Ala Ala Gly Val
    290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
```

```
            355                 360                 365
Asn Thr Leu Leu Val Pro Ser Leu Lys Arg Gly Val Ile Phe Arg Ile
        370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
            405                 410                 415

Asn Val Leu Tyr Val Leu Thr Asp Thr Ala Gly Asn Val Gln Lys Asp
            420                 425                 430

Asp Gly Ser Val Thr Asn Thr Leu Glu Asn Pro Gly Ser Leu Ile Lys
            435                 440                 445

Phe Thr Tyr Lys Ala Lys
    450

<210> SEQ ID NO 2
<211> LENGTH: 1612
<212> TYPE: DNA
<213> ORGANISM: Acinetobacter calcoaceticus

<400> SEQUENCE: 2
agctactttt atgcaacaga gcctttcaga aatttagatt ttaatagatt cgttattcat      60
cataatacaa atcatataga gaactcgtac aaacccttta ttagaggttt aaaaattctc     120
ggaaaatttt gacaatttat aaggtggaca catgaataaa catttattgg ctaaaattgc     180
tttattaagc gctgttcagc tagttacact ctcagcattt gctgatgttc ctctaactcc     240
atctcaattt gctaaagcga atcagagaa ctttgacaag aaagttattc tatctaatct     300
aaataagccg catgctttgt tatggggacc agataatcaa atttggttaa ctgagcgagc     360
aacaggtaag attctaagag ttaatccaga gtcgggtagt gtaaaaacag ttttcaggt     420 accagagatt gtcaatgatg ctgatgggca gaatggttta ttaggttttg ccttccatcc     480
tgattttaaa aataatcctt atatctatat ttcaggtaca tttaaaaatc cgaaatctac     540
agataaagaa ttaccgaacc aaacgattat tcgtcgttat acctataata atcaacaga     600 tacgctcgag aagccagtcg atttattagc aggattacct tcatcaaaag accatcagtc     660
aggtcgtctt gtcattgggc cagatcaaaa gatttattat acgattggtg accaagggcg     720
taaccagctt gcttatttgt tcttgccaaa tcaagcacaa catacgccaa ctcaacaaga     780
actgaatggt aaagactatc acacctatat gggtaaagta ctacgcttaa atcttgatgg     840
aagtattcca aaggataatc caagttttaa cggggtggtt agccatattt atacacttgg     900
acatcgtaat ccgcagggct tagcattcac tccaaatggt aaattattgc agtctgaaca     960
aggcccaaac tctgacgatg aaattaacct cattgtcaaa ggtggcaatt atggttggcc    1020
gaatgtagca ggttataaag atgatagtgg ctatgcttat gcaaattatt cagcagcagc    1080
caataagtca attaaggatt tagctcaaaa tggagtaaaa gtagccgcag ggtccctgt    1140 gacgaaagaa tctgaatgga ctggtaaaaa ctttgtccca ccattaaaaa ctttatatac    1200
cgttcaagat acctacaact ataacgatcc aacttgtgga gagatgacct acatttgctg    1260
gccaacagtt gcaccgtcat ctgcctatgt ctataagggc ggtaaaaaag caattactgg    1320
ttgggaaaat acattattgg ttccatcttt aaaacgtggt gtcattttcc gtattaagtt    1380
agatccaact tatagcacta cttatgatga cgctgtaccg atgtttaaga gcaacaaccg    1440
ttatcgtgat gtgattgcaa gtccagatgg gaatgtctta tatgtattaa ctgatactgc    1500
cggaaatgtc caaaaagatg atggctcagt aacaaataca ttagaaaacc caggatctct    1560
```
cattaagttc acctataagg ctaagtaata cagtcgcatt aaaaaaccga tc            1612

<210> SEQ ID NO 3
<211> LENGTH: 22
<212> TYPE: PRT
<213> ORGANISM: Acinetobacter calcoaceticus
<220> FEATURE:
<221> NAME/KEY: MISC_FEATURE
<222> LOCATION: (10)..(10)
<223> OTHER INFORMATION: Xaa is any natural amino acid residue
<221> NAME/KEY: MISC_FEATURE
<222> LOCATION: (11)..(11)
<223> OTHER INFORMATION: Xaa is any natural amino acid residue; however,
      it is not Ile when the Xaa at residue 10 is Glu.

<400> SEQUENCE: 3

Ser Glu Gln Gly Pro Asn Ser Asp Asp Xaa Xaa Asn Leu Ile Val Lys
1               5                   10                  15

Gly Gly Asn Tyr Gly Trp
            20

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 4
gaggttaatt gcatcgtcag ag                                              22

<210> SEQ ID NO 5
<211> LENGTH: 30
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 5
caatgaggtt aatgttatcg tcagagtttg                                      30

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 6
gaggttaata tcatcgtcag ag                                              22

<210> SEQ ID NO 7
<211> LENGTH: 22
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 7
gaggttaatt ttatcgtcag ag                                              22

<210> SEQ ID NO 8

```
<211> LENGTH: 30
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 8
caatgaggtt aatgtgatcg tcagagtttg                                  30

<210> SEQ ID NO 9
<211> LENGTH: 22
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 9
gaggttaatt tgatcgtcag ag                                          22

<210> SEQ ID NO 10
<211> LENGTH: 30
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 10
caatgaggtt aattacatcg tcagagtttg                                  30

<210> SEQ ID NO 11
<211> LENGTH: 22
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 11
gaggttaatt ccatcgtcag ag                                          22

<210> SEQ ID NO 12
<211> LENGTH: 26
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 12
caatgaggtt gaattcatcg tcagag                                      26

<210> SEQ ID NO 13
<211> LENGTH: 30
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 13
gacaatgagg tgaatttcat cgtcagagtt                                  30

<210> SEQ ID NO 14
<211> LENGTH: 21
```

```
<212> TYPE: PRT
<213> ORGANISM: Acinetobacter calcoaceticus
<220> FEATURE:
<221> NAME/KEY: MISC_FEATURE
<222> LOCATION: (1)..(1)
<223> OTHER INFORMATION: Xaa is any natural amino acid; however, it is
      not Asp when Xaa at residue 5 is Asn, Xaa at residue 8 is Lys, Xaa
      at residue 9 is Asp, Xaa at residue 10 is Asp, and Xaa at residue
      15 is Asn
<221> NAME/KEY: MISC_FEATURE
<222> LOCATION: (5)..(21)
<223> OTHER INFORMATION: Any Xaa is any natural amino acid

<400> SEQUENCE: 14

Xaa Thr Ala Gly Xaa Val Gln Xaa Xaa Xaa Gly Ser Val Thr Xaa Thr
1               5                   10                  15

Leu Glu Asn Pro Gly
            20

<210> SEQ ID NO 15
<211> LENGTH: 27
<212> TYPE: DNA
<213> ORGANISM: Artificial Sequence
<220> FEATURE:
<223> OTHER INFORMATION: synthetic oligonucleotide target primer used
      for mutagenesis of DNA derived from Acinetobacter calcoaceticus

<400> SEQUENCE: 15 catcttttttg gacatgtccg gcagtat                                         27
```